(12) United States Patent
Yoshihara et al.

(10) Patent No.: US 7,985,410 B2
(45) Date of Patent: Jul. 26, 2011

(54) **METHOD OR AGENT FOR INHIBITING THE FUNCTION OF EFFLUX PUMP *PSEUDOMONAS AERUGINOSA***

(75) Inventors: Eisaku Yoshihara, Kanagawa (JP);
Hidatoshi Inoko, Kanagawa (JP)

(73) Assignee: Tokai University, Kanagawa (JP)

( * ) Notice: Subject to any disclaimer, the term of this patent is extended or adjusted under 35 U.S.C. 154(b) by 0 days.

(21) Appl. No.: 12/161,557

(22) PCT Filed: Feb. 9, 2007

(86) PCT No.: PCT/JP2007/000072
§ 371 (c)(1),
(2), (4) Date: Dec. 19, 2008

(87) PCT Pub. No.: WO2007/091395
PCT Pub. Date: Aug. 16, 2007

(65) Prior Publication Data
US 2009/0221097 A1    Sep. 3, 2009

(30) Foreign Application Priority Data

Feb. 10, 2006   (JP) ................................. 2006-033522

(51) Int. Cl.
*A61K 39/40*    (2006.01)
(52) U.S. Cl. .................... 424/150.1; 530/388.4
(58) Field of Classification Search .......................... None
See application file for complete search history.

(56) References Cited

U.S. PATENT DOCUMENTS
2003/0092720 A1 * 5/2003 Nakayama et al. ...... 514/259.41

FOREIGN PATENT DOCUMENTS
| | | |
|---|---|---|
| JP | 2002510463 | 4/2002 |
| JP | 2003511074 | 3/2003 |
| WO | W09961021 | 12/1999 |

OTHER PUBLICATIONS

Gotoh et al (Antimicrobial Agents and Chemotherapy, 42(8):1938-1943, 1998).*
Gotoh et al (FEMS Microbiology Letters, 122(3):309-312, 1994).*
Jo, et al., Aminoglycoside Efflux in *Pseudomonas aeruginosa*: Involvement of Novel Outer Membrane Proteins, Antimicrobial Agents and Chemotherapy, Mar. 2003, p. 1101-1111, vol. 47, No. 3.
Li, et al., Mutational analysis of the OprM outer membrane component of the MexA-MexB-OprM multidrug efflux system of *Pseudomonas aeruginosa*, J Bacteriol. Jan. 2001;183(1), p. 12-27.
Wong, et al., Insertion Mutagenesis and Membrane Topology Model of the *Pseudomonas aeruginosa* Outer Membrane Protein OprM, Journal of Bacteriology, May 2000, p. 2402-2410, vol. 182, No. 9.
Wong, et al., Evaluation of a Structural Model of *Pseudomonas aeruginosa* Outer Membrane Protein OprM, an Efflux Component Involved in Intrinsic Antibiotic Resistance, Journal of Bacteriology, Jan. 2001, p. 367-374, vol. 183, No. 1.
Akama, et al., Crystal structure of the drug discharge outer membrane protein, OprM, of *Pseudomonas aeruginosa*: dual modes of membrane anchoring and occluded cavity end., J Biol Chem. Dec. 17, 2004; 279 (51):52816-52819.

* cited by examiner

*Primary Examiner* — Patricia A Duffy
(74) *Attorney, Agent, or Firm* — Carol L. Franis; Bozicevic, Field & Francis, LLP

(57) ABSTRACT

The purpose of the present invention is to provide a method and an agent to efficiently inhibit the function of the drug efflux pump of *Pseudomonas aeruginosa*. The invention provides a method to inhibit the function of the drug efflux pump of *Pseudomonas aeruginosa*, comprising modifying any amino acid residue selected from 100th to 109th or 311th to 320th amino acid residues in the amino acid sequence of mature OprM protein. The invention also provides an agent having such inhibitory effect, and a screening method thereof.

10 Claims, 1 Drawing Sheet

[Fig. 1]
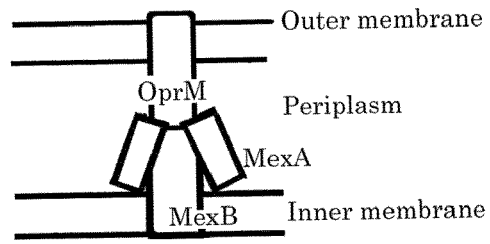
[Fig. 2]
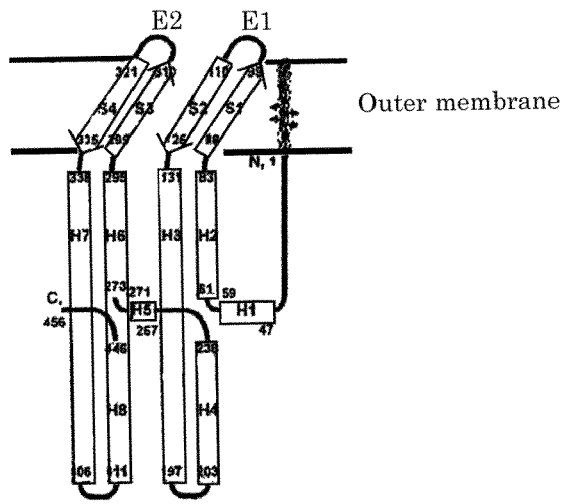
[Fig. 3]
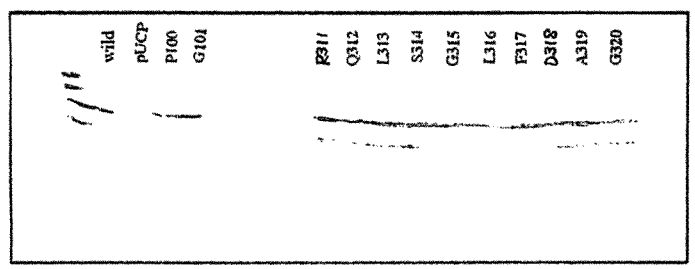

METHOD OR AGENT FOR INHIBITING THE FUNCTION OF EFFLUX PUMP *PSEUDOMONAS AERUGINOSA*

TECHNICAL FIELD

The present invention relates to a method to inhibit the function of the drug efflux pump of multiple drug resistant *Pseudomonas aeruginosa*. Particularly, the invention relates to a method to inhibit the function of the drug efflux pump of *Pseudomonas aeruginosa* in order to enhance the effect of antibiotics, by modifying amino acid sequence of OprM, which is a subunit of the drug efflux pump. The invention also relates to an agent having such effect, and a screening method of such agent.

BACKGROUND ART

*Pseudomonas aeruginosa*, as well as methicillin resistant *Staphylococcus aureus* MRSA, is one of major causative organisms of nosocomial infections. Since these bacteria have multidrug resistance, the treatment of these bacterial infections is difficult, presenting a serious problem in clinical settings. These bacteria acquire drug resistance by drug efflux pump. This pump uses energy to actively transport and discharge drug that has entered inside of the bacteria. Since the drug efflux pump of *Pseudomonas aeruginosa* can discharge a variety of antibiotics with different structures, *Pseudomonas aeruginosa* is resistant to a variety of drugs.

*Pseudomonas aeruginosa* is gram negative bacteria with two membranes, outer membrane and inner membrane. In order for drug to be discharged, the drug must be actively transported via these two membranes. The drug efflux pumps are classified into several families. Among them, pumps of RND (resistance nodulation division) family consist of three subunits. *Pseudomonas aeruginosa* has a plurality of RND pumps. Among them, the major pump is MexAB-OprM pump.

As schematically shown in FIG. 1, a MexAB-OprM pump has drug transporter MexB in the inner membrane, and OprM that forms a pore to transmit drug in the outer membrane. These membranes form a complex where MexA connecting the inner and the outer membrane exists in periplasm. Drug in the cell is directly discharged via this complex.

The amino acid sequence of the protein constituting MexAB-OprM pump has already been determined, and its conformation is being investigated using various methods including X-ray analysis (non-patent document 1). Attempts have been made to inhibit the pump function in order to enhance the effect of antibiotics. For example, in patent document 1, pharmacophore that is predicted by the relation between conformation and inhibitory effect of a compound that is expected to inhibit the pump is identified, and synthesis of a compound that satisfies the condition necessary for the pharmacophore is being attempted. However, this method is not practical because it involves screening of an immense number of compounds in order to identify a compound that can inhibit the pump function.

Non-patent document 1: Hiroyuki Akama et al., J. Biological Chemistry, Vol. 279, 52816-52819 (2004).
Patent document 1: Japanese published unexamined application 2002-128768

DISCLOSURE OF THE INVENTION

Problems to be Solved by the Invention

Therefore, the purpose of the invention is to establish a method to efficiently inhibit the function of the drug efflux pump of *Pseudomonas aeruginosa*, based on the amino acid sequence and conformation of the protein constituting the pump, and to provide an agent having such effect and a screening method thereof.

Means for Solving the Problem

In order to solve the problem as above, the inventors focus attention on the configuration of MexAB-OprM pump. Particularly, the inventors make use of the fact that all of three subunits constituting MexAB-OprM pump are indispensable for the function of the pump. When the function of any subunit is inhibited, the function of the pump as a whole may disappears. Based on this insight, the inventors find that the function of the drug efflux pump can be inhibited by modifying the amino acid sequence of OprM that has extracellular domain.

The invention provides a method to inhibit the function of the drug efflux pump of multi drug resistant *Pseudomonas aeruginosa*, by modifying any amino acids residues selected from 100th to 109th or 311th to 320th amino acid residues in the amino acid sequence of mature OprM protein.

Particularly, when inhibiting the function of MexAB-OprM pump, it is desirable to modify the 311th and/or the 318th amino acid residue in the amino acid sequence of mature OprM protein.

Effects of the Invention

According to the invention, an agent can be designed that inhibit the function of the drug efflux pump, based on the amino acid sequence of some domains of OprM, which is one of the subunits of the drug efflux pump. The method according to the invention facilitates designing and screening of a drug that can reduce drug resistance of *Pseudomonas aeruginosa* and enhance effect of antibiotics, without need of screening an immense number of compounds, which is indispensable in conventional rational drug designing that uses relationship between conformation and function. Thus, the invention can contribute to effective prevention and treatment of infections.

BRIEF DESCRIPTION OF THE DRAWINGS

FIG. 1 schematically shows the structure of MexAB-OprM pump.
FIG. 2 schematically shows the secondary structure of OprM.
FIG. 3 shows the result of western blotting to observe expression of OprM mutant in an embodiment.

BEST MODE FOR CARRYING OUT THE INVENTION

As described above, OprM, one of the subunits constituting MexAB-OprM pump, is a membrane protein that forms a channel for discharging drug via outer membrane. OprM consists of three major domains. FIG. 2 schematically shows the secondary structure of OprM. The characteristic large Domain 1 comprises mainly α helixes, and projects to periplasm. This domain is considered to interact with MexA or MexB. Domain 2 has a barrel-shaped structure of β sheets, and penetrates the outer membrane through which antibiotic passes. Domain 3 is the smallest domain comprising extracellular loops. This Domain 3 comprises two loops each of which has 10 amino acids.

The inventors focused attention on these loop domains, and investigated the role of this domain in the drug efflux function of the bacteria. Methods generally used in molecular biology were used in this study. Particularly, an amino acid residue in the loop was specifically replaced by other amino acid (cysteine residue), and the resultant mutant was returned to *Pseudomonas aeruginosa* to examine any change in the function of the drug efflux pump. With this procedure, we clarified if or not the amino acid is involved in the drug efflux function of the bacteria.

The two loops constituting OprM are referred to as E1 domain and E2 domain (FIG. 2). Their primary structures are as follows.

```
                                              (SEQ ID NO: 1)
E1: Pro-Gly-Asp-Leu-Ser-Thr-Thr-Gly-Ser-Pro (SEQ ID NO: 2)
E2: Arg-Gln-Leu-Ser-Gly-Leu-Phe-Asp-Ala-Gly
```

E1 is a sequence from the 100th amino acid proline to the 109th amino acid proline, and E2 is a sequence from the 311th amino acid arginine to the 320th amino acid glycine, in amino acid sequence of mature OprM.

Particularly, when aztreonam (AZD, β-1 lactam antibiotics) and nalidixic acid (NA) (quinolone antibiotics) were used as matrix (medicine), *Pseudomonas aeruginosa* in which E2 domain was modified, especially the bacteria in which mutants OprM (R311C), OprM (Q312C), OprM (F317C), OprM (R318c), OprM (A319C) or OprM (G320C) was introduced, showed altered drug sensitivity. Particularly, OprM (311C) markedly reduced resistance of the bacteria to AZT and NA, while OprM (D318C) markedly reduced resistance to AZT but did not reduce resistance to NA. The bacteria with OprM mutant have resistance to NA similar to that of wild type.

On the other hand, OprM (P109C) mutant in which the 109th amino acid was replaced by cysteine in ten residues in E1 domain showed enhanced drug sensitivity especially to NA. The above result demonstrates that amino acid sequence in E1 and E2 domains especially that in E2 domain plays an important role in the function of the drug efflux pump MexAB-OprM. Furthermore, the experiment indicates that the 311th arginine and the 318th aspartic acid in E2 domain play an essential role in the function of the drug efflux pump. In other words, it is found out that by replacing the amino acid in E2 domain, especially by replacing the 311th arginine and the 318th aspartic acid, the drug sensitivity of *Pseudomonas aeruginosa* can be enhanced (lowered drug resistance).

Arginine is a positively charged amino acid while aspartic acid is a negatively charged amino acid. The charge of the 311th and the 318th amino acids may be involved in the function of the drug efflux pump. In this specification, OprM (R311C) represents a mutant in which the 311th arginine (R) is replaced by cysteine (C).

The above finding shows that amino acids in E1 and E2 domains, especially the 311th arginine and the 318th aspartic acid in the amino acid sequence of mature OprM protein play an important role in the function of MexAB-OprM pump. Therefore, an agent specifically acting on these amino acids can inhibit the function of MexAB-OprM pump. The invention provides an agent having such effect.

An agent according to the invention acts on the sequence comprising any amino acid residue selected from the 100th to the 109th or the 311th to the 320th amino acid residue in the amino acid sequence of mature OprM protein to inhibit the function of the drug efflux pump of *Pseudomonas aeruginosa*. Preferably, the agent specifically acts on the sequence comprising any amino acid residue selected from the 311th and/or the 318th amino acid residue in the amino acid sequence of mature OprM protein.

In one aspect of the invention, an antibody that has above effect is provided. It is expected that the antibody specifically binds and blocks the amino acid domain as above to inhibit the function of MexAB-OprM pump.

Since the amino acid sequence of mature OprM protein has been identified, an antibody can be readily prepared by synthesizing polypeptide having an amino acid sequence identical or homologous to the relevant sequence, and using other methods well known in molecular biology.

For example, like conventional antibody therapy, a mechanism can be devised in which antibody bound to *Pseudomonas aeruginosa* exerts antimicrobial effect via complement system. However, based on the inventor's finding, the antibody can inhibit the pump function only by binding to the target amino acid domain. Therefore, the antibody is effective even when a complement system cannot be mobilized.

The inventors actually prepared a monoclonal antibody to the polypeptide having the amino acid sequence of E2 domain (SEQ ID NO: 2) and administered the monoclonal antibody together with an antibiotic. This experiment confirmed that in the presence of this antibody, the efficacy of the antibiotic is enhanced, resulting in marked reduction in the viable count of bacteria compared to the antibiotic without the antibody (control).

The Fc domain of the antibody is not directly involved in binding to substrate, a fragment of antibody lacking Fc domain can be used as an agent according to the first embodiment of the invention. Since the mass of the antibody can be reduced when it lacks Fc, the antibody can access to the *Pseudomonas aeruginosa* more effectively, which improves effect of the agent.

Given that the agent is to be administered to human, a humanized antibody that has human antibody is advantageous.

The second aspect of the invention provides organic small molecule. Since the inventors have identified the target amino acid sequence and its position, a small peptide or other organic molecule can be screened that can specifically bind to the sequence. Therefore, the invention provides a screening method of an agent which inhibits the function of the drug efflux pump of *Pseudomonas aeruginosa*, comprising contacting test substances and a polypeptide having amino acid sequence of SEQ ID NO: 1 or 2, and selecting test substances that interact with the polypeptide. Once an agent (test substance) having such effect is identified, its effect on the drug efflux pump of *Pseudomonas aeruginosa* can be examined by conventional in vivo or in vitro procedure.

Alternatively, since the three-dimensional structure of MexAB-OprM pump and OprM have been elucidated, the drug according to the invention can be prepared by identifying the target domain of the MexAB-OprM pump or OprM, estimating a compound having a conformation that can cover the target domain by using computer program, synthesizing a compound based on the result and screening its effect.

Although MexAB-OprM is known as a multidrug efflux pump that is constitutively expressed in *Pseudomonas aeruginosa* and contributes to drug resistance thereof, there is another efflux pump that is inducible by specific drug. One example is MexXY-OprM pump. The expression of this efflux pump is induced by aminoglycoside antibiotics such as gentamicin, and the pump endows the bacteria with the resistance to these drugs. Like MexAB-OprM, MexXY-OprM comprises three subunits, and has same OprM in its outer membrane. Therefore, it is expected that MexXY-OprM pump can also be inhibited by the same mechanism as MexAB-OprM.

In fact, *Pseudomonas-aeruginosa* strain lacking MexAB-OprM is susceptible to aminoglycoside antibiotics. When wild type OprM is introduced in the strain, resistance to aminoglycoside antibiotics recovers. This observation indicates that when MexXY is induced by aminoglycoside antibiotics, the bacteria is susceptible to the antibiotics because it lacks its pump function due to absence of OprM, but when OprM is introduced, the pump function recovers.

When a mutant of OprM (one amino acid in E1 and E2 domains, respectively, is replaced by cysteine) similar to that used in MexAB-OprM is introduced to *Pseudomonas aeruginosa* lacking MexAB-OprM, the pump function was reduced in the *Pseudomonas aeruginosa* having amino acid replacement in E1 domain, in contrast to MexAB-OprM (data is not shown). That is, not only amino acid replacement in E2 domain which has marked effect on MexAB-OprM, but also replacement in E1 domain can have inhibitory effect on the pump function of *Pseudomonas aeruginosa*.

As described, the above agent inhibits the function of the drug efflux pump of *Pseudomonas aeruginosa*. Thus, when it is co-administered with antibiotics conventionally used for prevention/treatment of *Pseudomonas aeruginosa* infection, it can maintain the effect of antibiotics. That is, preferably the agent according to the invention is provided in a combination with antibody. When the agent according to the invention is combined with antibody, it can effectively prevent/treat *Pseudomonas aeruginosa* infection. It goes without saying that the agent according to the invention may contain other ingredient such as pharmaceutically acceptable carrier, solvent, excipient or diluent, besides the antibiotics. Next, some of embodiments of the invention will be described in detail. It should be noted, however, the following embodiment should not be construed to limit the range of the invention.

EMBODIMENTS

Embodiment 1

Mutant protein was prepared in which 20 amino acid residues were replaced by cysteine residues, respectively, in E1 and E2 domains of the amino acid sequence of mature OprM protein as above. First, OprM gene was introduced into pUCP20 as a vector. This vector is a shuttle vector which works in *Escherichia coli* and *Pseudomonas aeruginosa*. Specific mutation was introduced to OprM gene by using regular mutation introducing kit, and resultant vector was transformed into *E. coli*. The resultant *E. coli* was cultured to prepare plasmid, and the sequence of the plasmid was determined to confirm that the mutation was successfully introduced.

Next, the plasmid was introduced into the *Pseudomonas aeruginosa* lacking OprM, and the drug sensitivity of the resultant bacteria was determined to evaluate the pump function thereof. Drug sensitivity might be enhanced if the function of the pump was inhibited. Drug sensitivity was indicated by minimum inhibitory concentration (MIC). Aztreonam (AZT) (β-1 lactam antibiotic) and nalidixic acid (NA) (qunolone antibiotic) were used as drugs. The result is shown in the following Table 1.

TABLE 1

| OprM mutant | MIC for AZT (µg/ml) | MIC for NA (µg/ml) |
|---|---|---|
| OprM (wild type) | 3.13 | 50 |
| OprM (P100C) | 3.13 | 50 |
| OprM (G101C) | 3.13 | 50 |
| OprM (D102C) | 3.13 | 50 |
| OprM (L103C) | 3.13 | 50 |
| OprM (S104C) | 3.13 | 50 |
| OprM (T105C) | 3.13 | 50 |
| OprM (T106C) | 3.13 | 50 |
| OprM (G107C) | 3.13 | 50 |
| OprM (S108C) | 3.13 | 50 |
| OprM (P109C) | 3.13 | 3.13 |
| OprM (R311C) | 0.39 | 6.25 |
| OprM (Q312C) | 0.78 | 25 |
| OprM (L313C) | 3.13 | 50 |
| OprM (S314C) | 3.13 | 50 |
| OprM (G315C) | 0.78 | 25 |
| OprM (L316C) | 3.13 | 50 |
| OprM (F317C) | 1.54 | 50 |
| OprM (D318C) | 0.39 | 25 |
| OprM (A319C) | 1.54 | 50 |
| OprM (G320C) | 1.54 | 50 |

As shown in the table, the sensitivity to NA markedly changes when the 109th amino acid in E1 domain is replaced. A plurality of mutants which has amino acid replacement in E2 domain show marked change in drug sensitivity. That is, the replaced amino acids play an important role in the pump function of the bacteria.

The above experiment demonstrated that the mutants having amino acid replacement in E2 domain show altered pump function depending on the replacement site. In order to confirm that this result was not caused by absence of expression of the mutant, an experiment was conducted to confirm that every mutant is actually expressed. Particularly, *Pseudomonas aeruginosa* having mutants and *Pseudomonas aeruginosa* having plasmid with wild type OprM, respectively, were cultured in the presence of IPTG that induces expression of gene on the plasmid, then harvested. The result of Western blotting is shown in FIG. 3. FIG. 3 shows that mutants were actually expressed.

Embodiment 2

Inhibition of the Drug Efflux Pump of *Pseudomonas aeruginosa* by Monoclonal Antibody to E2 Domain of OprM (1) Preparation of Monoclonal Antibody Polypeptide having same amino acid sequence as E2 of OprM was synthesized. A mouse was immunized with this polypeptide as antigen to prepare monoclonal antibody.

The culture supernatant was prepared from the cells producing antibody reactive to the polypeptide. The supernatant was loaded on the protein G column to purify 17 types of monoclonal antibodies.

(2) Measurement of the Inhibitory Effect of Monoclonal Antibody on the Drug Efflux Pump of MexAB-OprM From 17 types of monoclonal antibodies prepared in the step (1), 2 types (MAb1 and MAb2) were selected and used in the following experiment.

Test bacteria: Precultured *Pseudomonas aeruginosa* PA01 strain was diluted in Mueller Hinton(MH) broth, incubated at 37° C. until absorbance at 600 nm reached to about 0.8. The cell suspension was diluted 200 fold with MH broth for use in the experiment.

To 20 µl of *Pseudomonas aeruginosa* suspension, 25 µl of monoclonal antibody solution was added and the resultant mixture was incubated at 37° C. for 30 minutes. 5 µl of aztreonam (AZT) (10 µg/ml) solution was added as an antibiotic (the final concentration of AZT was 1.0 µg/ml), and reacted at 37° C. for 60 minutes. In order to evaluate the effect of the antibody, antibody solution heated to 100° C. for 5 minutes was used as a control.

Determination of Viable Count

To 50 µl of the mixture, 950 µl of cold saline (PBS) was added, and 50 µl of the resultant solution was added to 950 µl of PBS. 100 µl of the solution was removed therefrom, applied on LB agar and incubated at 37° C. overnight. The colonies grown on agar were counted on the next day.

The viable count obtained in the presence of monoclonal antibody and that obtained in the absence of antibody were represented in percentage to evaluate the effect of the antibody. The result was as follows.

TABLE 2

| Monoclonal antibody | Percentage of viable count |
| --- | --- |
| MAb1 | 57.2 ± 17.2 |
| MAb2 | 56.9 ± 18.7 |

As shown in FIG. 2, the monoclonal antibodies (MAb1 and MAb2) inhibited the drug efflux pump to suppress the discharge of the antibody, which, in turn, enhanced antimicrobial effect of the antibody. It was confirmed that these monoclonal antibodies have inhibitory effect on the drug efflux pump MexAB-OprM.

The invention claimed is:

1. An agent for inhibiting the function of the drug efflux pump MexAB-OprM of *Pseudomonas aeruginosa*, the agent comprising a monoclonal antibody, or fragment thereof, that specifically binds to the amino acid sequence represented by SEQ ID NO: 2.

2. The agent according to claim 1, wherein the monoclonal antibody, or fragment thereof, specifically binds to the amino acid sequence represented by SEQ ID NO: 2 comprising the 311th and/or the 318th amino acid residues in the amino acid sequence of mature OprM protein (SEQ ID NO:3).

3. The agent according to claim 1, wherein the agent comprises the monoclonal antibody.

4. An agent for treatment of *Pseudomonas aeruginosa* infection comprising the agent according to claim 1 and an antibiotic.

5. The agent according to claim 2, wherein the agent comprises the monoclonal antibody.

6. An agent for treatment of *Pseudomonas aeruginosa* infection comprising the agent according to claim 2 and an antibiotic.

7. The agent according to claim 1, wherein the agent comprises a monoclonal antibody fragment that specifically binds to the amino acid sequence represented by SEQ ID NO: 2.

8. The agent according to claim 7, wherein the antibody fragment lacks an Fc domain.

9. The agent according to claim 2, wherein the agent comprises a monoclonal antibody fragment that specifically binds to the amino acid sequence represented by SEQ ID NO: 2 comprising the 311$^{th}$ and/or the 318$^{th}$ amino acid residues in the amino acid sequence of mature OprM protein (SEQ ID NO:3).

10. The agent according to claim 9, wherein the antibody fragment lacks an Fc domain.

\* \* \* \* \*

UNITED STATES PATENT AND TRADEMARK OFFICE
CERTIFICATE OF CORRECTION

| | | |
|---|---|---|
| PATENT NO. | : 7,985,410 B2 | Page 1 of 1 |
| APPLICATION NO. | : 12/161557 | |
| DATED | : July 26, 2011 | |
| INVENTOR(S) | : Eisaku Yoshihara et al. | |

It is certified that error appears in the above-identified patent and that said Letters Patent is hereby corrected as shown below:

On the Title Page Item (54) and Col. 1, line 1, in the Title, please insert --of-- so that it reads --Method of Agent for Inhibiting the Function of Efflux Pump of *Pseudomonas Aeruginosa*--.

Signed and Sealed this
Sixth Day of March, 2012

David J. Kappos
*Director of the United States Patent and Trademark Office*

```
SEQUENCE LISTING

<160> NUMBER OF SEQ ID NOS: 3

<210> SEQ ID NO 1
<211> LENGTH: 10
<212> TYPE: PRT
<213> ORGANISM: Pseudomonas aeruginosa

<400> SEQUENCE: 1

Pro Gly Asp Leu Ser Thr Thr Gly Ser Pro
1               5                   10

<210> SEQ ID NO 2
<211> LENGTH: 10
<212> TYPE: PRT
<213> ORGANISM: Pseudomonas aeruginosa

<400> SEQUENCE: 2

Arg Gln Leu Ser Gly Leu Phe Asp Ala Gly
1               5                   10

<210> SEQ ID NO 3
<211> LENGTH: 468
<212> TYPE: PRT
<213> ORGANISM: Pseudomonas aeruginosa

<400> SEQUENCE: 3

Cys Ser Leu Ile Pro Asp Tyr Gln Arg Pro Glu Ala Pro Val Ala Ala
1               5                   10                  15

Ala Tyr Pro Gln Gly Gln Ala Tyr Gly Gln Asn Thr Gly Ala Ala Ala
            20                  25                  30

Val Pro Ala Ala Asp Ile Gly Trp Arg Glu Phe Phe Arg Asp Pro Gln
        35                  40                  45

Leu Gln Gln Leu Ile Gly Val Ala Leu Glu Asn Asn Arg Asp Leu Arg
    50                  55                  60

Val Ala Ala Leu Asn Val Glu Ala Phe Arg Ala Gln Tyr Arg Ile Gln
65                  70                  75                  80

Arg Ala Asp Leu Phe Pro Arg Ile Gly Val Asp Gly Ser Gly Thr Arg
                85                  90                  95

Gln Arg Leu Pro Gly Asp Leu Ser Thr Thr Gly Ser Pro Ala Ile Ser
            100                 105                 110

Ser Gln Tyr Gly Val Thr Leu Gly Thr Thr Ala Trp Glu Leu Asp Leu
        115                 120                 125

Phe Gly Arg Leu Arg Ser Leu Arg Asp Gln Ala Leu Glu Gln Tyr Leu
    130                 135                 140
```

```
Ala Thr Glu Gln Ala Gln Arg Ser Ala Gln Thr Thr Leu Val Ala Ser
145                 150                 155                 160

Val Ala Thr Ala Tyr Leu Thr Leu Lys Ala Asp Gln Ala Gln Leu Gln
                165                 170                 175

Leu Thr Lys Asp Thr Leu Gly Thr Tyr Gln Lys Ser Phe Asp Leu Thr
            180                 185                 190

Gln Arg Ser Tyr Asp Val Gly Val Ala Ser Ala Leu Asp Leu Arg Gln
            195                 200                 205

Ala Gln Thr Ala Val Glu Gly Ala Arg Ala Thr Leu Ala Gln Tyr Thr
        210                 215                 220

Arg Leu Val Ala Gln Asp Gln Asn Ala Leu Val Leu Leu Leu Gly Ser
225                 230                 235                 240

Gly Ile Pro Ala Asn Leu Pro Gln Gly Leu Gly Leu Asp Gln Thr Leu
                245                 250                 255

Leu Thr Glu Val Pro Ala Gly Leu Pro Ser Asp Leu Leu Gln Arg Arg
            260                 265                 270

Pro Asp Ile Leu Glu Ala Glu His Gln Leu Met Ala Ala Asn Ala Ser
            275                 280                 285

Ile Gly Ala Ala Arg Ala Ala Phe Phe Pro Ser Ile Ser Leu Thr Ala
        290                 295                 300

Asn Ala Gly Thr Met Ser Arg Gln Leu Ser Gly Leu Phe Asp Ala Gly
305                 310                 315                 320

Ser Gly Ser Trp Leu Phe Gln Pro Ser Ile Asn Leu Pro Ile Phe Thr
            325                 330                 335

Ala Gly Ser Leu Arg Ala Ser Leu Asp Tyr Ala Lys Ile Gln Lys Asp
            340                 345                 350

Ile Asn Val Ala Gln Tyr Glu Lys Ala Ile Gln Thr Ala Phe Gln Glu
        355                 360                 365

Val Ala Asp Gly Leu Ala Ala Arg Gly Thr Phe Thr Glu Gln Leu Gln
        370                 375                 380

Ala Gln Arg Asp Leu Val Lys Ala Ser Asp Glu Tyr Tyr Gln Leu Ala
385                 390                 395                 400

Asp Lys Arg Tyr Arg Thr Gly Val Asp Asn Tyr Leu Thr Leu Leu Asp
                405                 410                 415

Ala Gln Arg Ser Leu Phe Thr Ala Gln Gln Gln Leu Ile Thr Asp Arg
            420                 425                 430

Leu Asn Gln Leu Thr Ser Glu Val Asn Leu Tyr Lys Ala Leu Gly Gly
        435                 440                 445

Gly Trp Asn Gln Gln Thr Val Thr Gln Gln Gln Thr Ala Lys Lys Glu
    450                 455                 460

Asp Pro Gln Ala
465
```